(12) United States Patent
Belko et al.

(10) Patent No.: US 8,557,827 B2
(45) Date of Patent: Oct. 15, 2013

(54) PYRIMIDINE DERIVATIVES AND THEIR USE IN PERFUME COMPOSITIONS

(75) Inventors: Robert P. Belko, Monroe, NJ (US); Anthony T. Levorse, Jr., Westfield, NJ (US); Anubhav P. S. Narula, Hazlet, NJ (US); Michael G. Monteleone, Hazlet, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 13/430,908

(22) Filed: Mar. 27, 2012

(65) Prior Publication Data

US 2012/0207698 A1 Aug. 16, 2012

Related U.S. Application Data

(63) Continuation-in-part of application No. 13/027,314, filed on Feb. 15, 2011.

(51) Int. Cl.
*C07D 471/00* (2006.01)
*C07D 239/70* (2006.01)

(52) U.S. Cl.
USPC .......................................... 514/257; 544/246

(58) Field of Classification Search
None
See application file for complete search history.

(56) References Cited

U.S. PATENT DOCUMENTS

2012/0207698 A1* 8/2012 Belko et al. .................. 424/76.2

* cited by examiner

*Primary Examiner* — Noble Jarrell
*Assistant Examiner* — John S Kenyon
(74) *Attorney, Agent, or Firm* — Elizabeth M. Quirk; XuFan Tseng; Joseph F. Leightner

(57) ABSTRACT

The present invention relates to novel pyrimidine derivatives and their use in perfume compositions. The novel pyrimidine derivatives of the present invention are represented by the following formula:

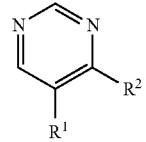

Structure I wherein when $R^1$ represents H, $R^2$ represents a substituted indanyl selected from the group consisting of

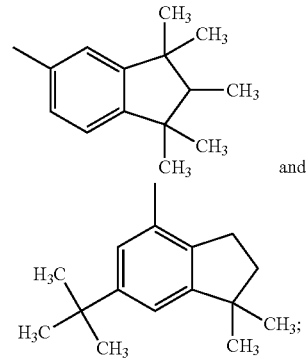

and or wherein $R^1$ and $R^2$ taken together represent a group of the formula:

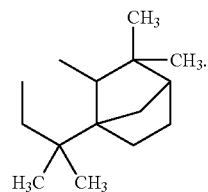

11 Claims, No Drawings

PYRIMIDINE DERIVATIVES AND THEIR USE IN PERFUME COMPOSITIONS

STATUS OF RELATED APPLICATIONS

This application is a continuation-in-part of U.S. Ser. No. 13/027,314, filed Feb. 15, 2011, now pending, the contents hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel compounds and their unexpected advantageous use in enhancing, improving or modifying the fragrance of perfumes, colognes, toilet water, fabric care products, personal products and the like.

More specifically, the present invention relates to novel pyrimidine derivatives represented by Structure I set forth below:

Structure I

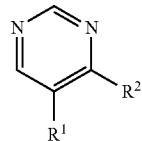

wherein when $R^1$ represents H, $R^2$ represents a substituted indanyl selected from the group consisting of

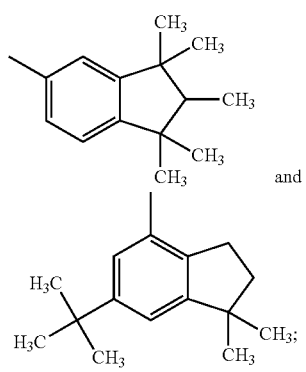

and or wherein $R^1$ and $R^2$ taken together represent a group of the formula:

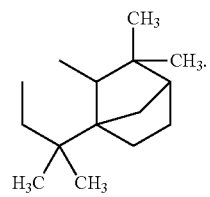

Another embodiment of the present invention relates to a fragrance composition comprising the novel compounds provided above.

Another embodiment of the present invention relates to a fragrance product comprising the compounds provided above.

Another embodiment of the present invention relates to a method of improving, enhancing or modifying a fragrance formulation through the addition of an olfactory acceptable amount of the novel compounds provided above.

These and other embodiments of the present invention will be apparent by reading the following specification.

DETAILED DESCRIPTION OF THE INVENTION

The compounds of the present invention may be represented by the following structures:

Structure II

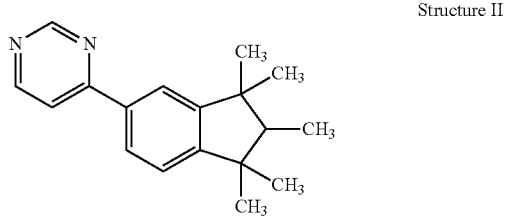

Structure III

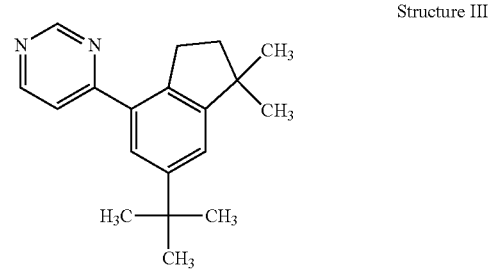

Structure IV

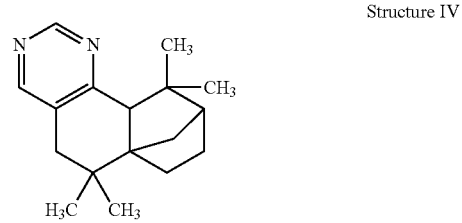 [SMILES: CC1(C)C2CCC3(C2)C1c1ncncc1CC3(C)C]

Those with the skill in the art will appreciate that

Structure II is 4-(2,3-dihydro-1,1,2,3,3-pentamethyl-1H-inden-5-yl)-pyrimidine;

Structure III is 4-[6-(1,1-dimethylethyl)-2,3-dihydro-1,1-dimethyl-1H-inden-4-yl]-pyrimidine; and Structure IV is 6,6,10,10-tetramethyl-5,7,8,9,10,10a-hexahydro-6H-6a,9-methanobenzo[H]quinazoline.

The compounds of the present invention can each be similarly prepared from a corresponding starting material that is commercially available. The generalized reaction scheme is depicted below, the details of which are specified in the Examples. Materials were purchased from Aldrich Chemical Company unless noted otherwise.

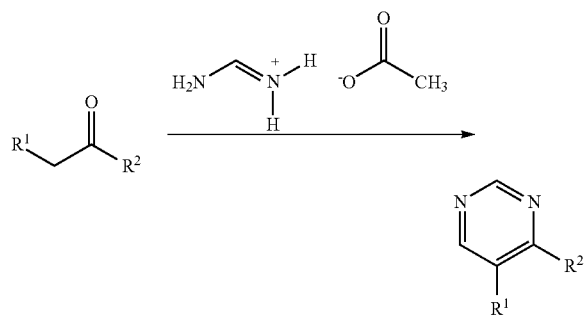

The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1, 3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1] hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methylpentyl) cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone a Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo [7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound as defined above.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation this ingredient provides musky, ambery, and powdery notes to make the fragrance formulation more desirable and noticeable, and add the perception of value. The odor qualities found in this material assist in beautifying and enhancing the finished accord as well as improving the performance of the other materials in the fragrance.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, mol is understood to be mole, and mmHg be millimeters (mm) of mercury (Hg). IFF as used in the examples is understood to mean International Flavors & Fragrances Inc., New York, N.Y., USA.

Example I

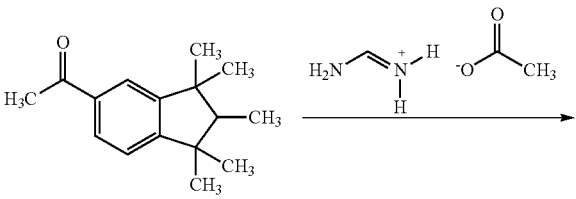

1,1,2,3,3-pentamethyl-5-indanyl methyl ketone

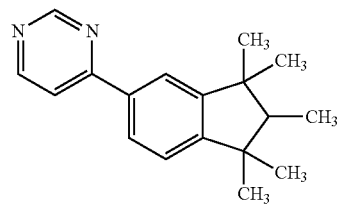

4-(2,3-dihydro-1,1,2,3,3-pentamethyl-1H-inden-5-yl)-pyrimidine

Preparation of 4-(2,3-dihydro-1,1,2,3,3-pentamethyl-1H-inden-5-yl)-pyrimidine (Structure II)

A 5 L reaction vessel was charged with 1,1,2,3,3-pentamethyl-5-indanyl methyl ketone (460 g, 2.0 mol) (commercially available at IFF), formamidine acetate (675 g, 6.4 mol), and butanol (1.0 L). The reaction mixture was heated to 120° C. for 10 hours and then cooled to 25° C. The reaction mixture was washed twice with brine (1 L) and purified by vacuum distillation to afford 4-(2,3-dihydro-1,1,2,3,3-pentamethyl-1H-inden-5-yl)-pyrimidine (200 g) having a boiling point of 153° C. at a pressure of 2.0 mmHg.

$^1$H NMR (CDCl$_3$, 500 MHz): 9.25 ppm (d, 1H, J=1.28 Hz), 8.71 ppm (d, 1H, J=5.40 Hz), 7.88-7.93 ppm (m, 2H), 7.69 (d, 1H, J=5.40 Hz, of d, J=1.40 Hz), 7.28 ppm (d, 1H, J=7.90 Hz, of d, J=0.40 Hz), 1.92 ppm (q, 1H, J=7.36 Hz), 1.35 ppm (s, 3H), 1.31 ppm (s, 3H), 1.13 ppm (s, 3H), 1.11 ppm (s, 3H), 1.02 ppm (d, 3H, J=7.36 Hz).

4-(2,3-Dihydro-1,1,2,3,3-pentamethyl-1H-inden-5-yl)-pyrimidine was described as having weak floral note.

Example II

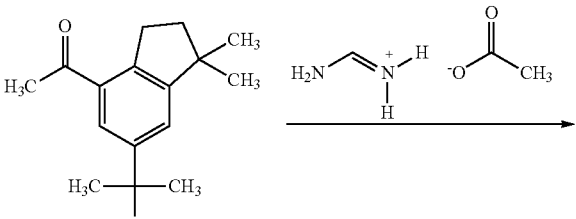

6-tert-butyl-1,1-dimethyl-4-indanyl methyl ketone

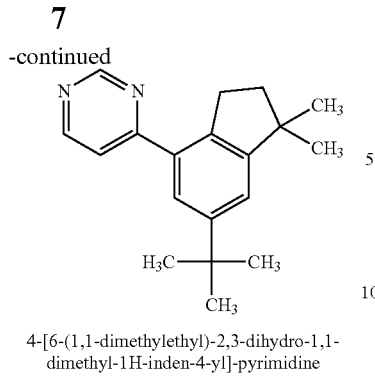

4-[6-(1,1-dimethylethyl)-2,3-dihydro-1,1-dimethyl-1H-inden-4-yl]-pyrimidine

Preparation of 4-[6-(1,1-dimethylethyl)-2,3-dihydro-1,1-dimethyl-1H-inden-4-yl]-pyrimidine (Structure III)

A 5 L reaction vessel was charged with 6-tert-butyl-1,1-dimethyl-4-indanyl methyl ketone (300 g, 1.2 mol) (commercially available at IFF), formamidine acetate (639 g, 6.1 mol), and butanol (1.0 L). The reaction mixture was heated to 125° C. for 10 hours and then cooled to 25° C. The reaction mixture was washed twice with brine (1 L) and purified by vacuum distillation to afford 4-[6-(1,1-dimethylethyl)-2,3-dihydro-1,1-dimethyl-1H-inden-4-yl]-pyrimidine (200 g) having a boiling point of 180° C. at a pressure of 0.5 mmHg.

$^1$H NMR (CDCl$_3$, 500 MHz): 9.28 ppm (d, 1H, J=1.28 Hz), 8.74 ppm (d, 1H, J=5.32 Hz), 7.65 ppm (d, 1H, J=1.84 Hz), 7.57 ppm (d, 1H, J=5.32 Hz, of d, J=1.44 Hz), 7.31 ppm (d, 1H, J=1.80 Hz), 3.11 ppm (t, 2H, J=7.14 Hz), 1.95 ppm (t, 2H, J=7.14 Hz), 1.38 ppm (s, 9H), 1.31 ppm (s, 6H).

4-[6-(1,1-Dimethylethyl)-2,3-dihydro-1,1-dimethyl-1H-inden-4-yl]-pyrimidine was described as having weak fatty note.

Example III

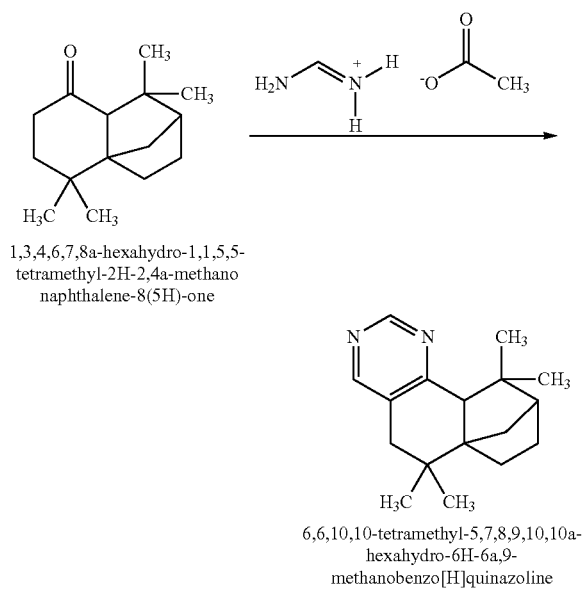

1,3,4,6,7,8a-hexahydro-1,1,5,5-tetramethyl-2H-2,4a-methano naphthalene-8(5H)-one 6,6,10,10-tetramethyl-5,7,8,9,10,10a-hexahydro-6H-6a,9-methanobenzo[H]quinazoline Preparation of 6,6,10,10-tetramethyl-5,7,8,9,10,10a-hexahydro-6H-6a,9-methanobenzo[H]quinazoline (Structure IV)

A 5 L reaction vessel was charged with 1,3,4,6,7,8a-hexahydro-1,1,5,5-tetramethyl-2H-2,4a-methanonaphthalene-8(5H)-one (440 g, 2.0 mol) (commercially available at IFF), formamidine acetate (1040 g, 10.0 mol) and butanol (2 L). The reaction mixture was heated to 120° C. for 10 hours and then cooled to 25° C. The reaction mixture was washed twice with brine (1 L) and purified by vacuum distillation to afford crude product 6,6,10,10-tetramethyl-5,7,8,9,10,10a-hexahydro-6H-6a,9-methanobenzo[H]quinazoline (430 g) having a boiling point of 159° C. at a pressure of 1.0 mmHg Further recrystallization from ethanol afforded 6,6,10,10-tetramethyl-5,7,8,9,10,10a-hexahydro-6H-6a,9-methanobenzo[H]quinazoline (95% purity) (125 g) with a melting point of 44-45° C.

$^1$H NMR (CDCl$_3$, 500 MHz): 8.97 ppm (d, 1H, J=0.60 Hz), 8.34 ppm (s, 1H), 2.81 ppm (d, 1H, J=16.14 Hz), 2.45 ppm (s, 1H), 2.30 ppm (d, 1H, J=16.11 Hz), 1.90-1.97 ppm (m, 1H), 1.76-1.77 ppm (m, 1H), 1.71 ppm (d, 1H, J=3.95 Hz, of t, J=12.22 Hz), 1.61-1.66 ppm (d, 1H, J=9.45 Hz, of m), 1.51-1.58 ppm (m, 1H), 1.39 ppm (s, 3H), 1.28 ppm (d, 1H, J=9.95 Hz, of t, J=1.68 Hz), 1.16-1.23 ppm (m, 1H), 1.09 ppm (s, 3H), 0.74 ppm (s, 3H), 0.67 ppm (s, 3H).

6,6,10,10-Tetramethyl-5,7,8,9,10,10a-hexahydro-6H-6a,9-methanobenzo[H]quinazoline was described as having musky, woody, and ambery notes.

Example IV

The fragrance formulas exemplified as follows demonstrated that the addition of 6,6,10,10-tetramethyl-5,7,8,9,10,10a-hexahydro-6H-6a, 9-methanobenzo[H]quinazoline (Structure IV) provided floral odor character with woody and musky undertones.

| Ingredient | Parts (g) | Parts (g) |
|---|---|---|
| Triplal BHT | 20 | 20 |
| Aldehyde C11 Ulenic | 13 | 13 |
| Aldehyde C12 MNA | 10 | 10 |
| Iso Gamma Super ™ | 170 | 170 |
| Hydroxy Citronellal Pure | 10 | 10 |
| Bacdanol ™ BHT | 10 | 10 |
| Benz Acetone | 25 | 25 |
| Benz Salicylate | 50 | 50 |
| Citronellol 950 | 15 | 15 |
| Cyclacet | 20 | 20 |
| Cyclaprop | 20 | 20 |
| Damascone delta | 2 | 2 |
| Dihydro myrcenol | 60 | 60 |
| Eugenol Natural | 10 | 10 |
| Galaxolide 50 ™ | 140 | 140 |
| Hexyl cinnamic ald | 35 | 35 |
| Hexyl Salicylate | 35 | 35 |
| Iso bornyl acetate | 40 | 40 |
| Iao butyl quinoline | 1 | 1 |
| Methyl ionone gamma | 15 | 15 |
| Peomosa ™ | 25 | 25 |
| Rosetone | 60 | 60 |
| Styralyl acetate | 1 | 1 |
| Terpineol alpha | 3 | 3 |
| Gamma undecalactone | 6 | 6 |
| Veramoss | 1 | 1 |
| Verdox | 40 | 40 |

-continued

| Ingredient | Parts (g) | Parts (g) |
|---|---|---|
| Yara Yara | 1 | 1 |
| Structure IV | 30 | — |
| DPG | — | 30 |
| Total | 868 | 868 |

Example V

The fragrance formula exemplified as follows demonstrated that 6,6,10,10-Tetramethyl-5,7,8,9,10,10a-hexahydro-6H-6a, 9-methanobenzo[H]quinazoline (Structure IV) imparted diffusive floral, soft powdery, and sweet characters.

| Ingredient | Parts (g) |
|---|---|
| Santaliff ™ | 24 |
| Phenoxanol ™ | 32 |
| Coumarin | 28 |
| Cyclamal Extra | 1 |
| Eth Vanillin | 7 |
| Geraniol 980 Pure | 1 s |
| Hedione ™ | 60 |
| Amy Cinnamic Aldehyde | 60 |
| Heliotropine | 17 |
| Hexyl Cinnamic Ald | 16 |
| Beta Ionone Extra | 6 |
| Iso E Super ™ | 70 |
| Lyral ™ | 16 |
| lillial ™ | 160 |
| Lilianth | 20 |
| Methyl Ionone Gamma A | 73 |
| Veramoss | 2 |
| Peru Balsam Oil India | 3 |
| Prenyl Acetate | 1 |
| Methyl Cedryl Ketone | 40 |
| Methyl Phenyl Acetate | 1 |
| Aubepine | 4 |
| Benzoin | 10 |
| Cedrol Tex | 3 |
| Citronellol Extra | 3 |
| Geraniol Coeur | 4 |
| Methyl Cinnamate | 3 |
| Styrax Alva Ess | 2 |
| Vanillin ex Lignin | 12 |
| Cananga Java Native | 5 |
| Structure IV | 20 |
| Total | 704 |

What is claimed is:

1. A compound of Structure IV:

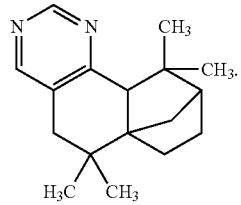

Structure IV

2. A fragrance formulation containing an olfactory acceptable amount of the compound of claim 1.

3. The fragrance formulation of claim 2 incorporated into a product selected from the group consisting of a perfume, a cologne, toilet water, a cosmetic product, a personal care product, a fabric care product, a cleaning product, and an air freshener.

4. The fragrance formulation of claim 3, wherein the cleaning product is selected from the group consisting of a detergent, a dishwashing composition, a scrubbing compound, and a window cleaner.

5. The fragrance formulation of claim 2, wherein the olfactory acceptable amount is from 0.005 to 50 weight percent of the fragrance formulation.

6. The fragrance formulation of claim 2, wherein the olfactory acceptable amount is from 0.5 to 25 weight percent of the fragrance formulation.

7. The fragrance formulation of claim 2, wherein the olfactory acceptable amount is from 1 to 10 weight percent of the fragrance formulation.

8. A method of improving, enhancing, or modifying a fragrance formulation through the addition of an olfactory acceptable amount of the compound of claim 1.

9. The method of claim 8, wherein the olfactory acceptable amount is from 0.005 to 50 weight percent of the fragrance formulation.

10. The method of claim 8, wherein the olfactory acceptable amount is from 0.5 to 25 weight percent of the fragrance formulation.

11. The method of claim 8, wherein the olfactory acceptable amount is from 1 to 10 weight percent of the fragrance formulation.

* * * * *